US012636110B2

(12) United States Patent
Kanazawa et al.

(10) Patent No.: US 12,636,110 B2
(45) Date of Patent: May 26, 2026

(54) SURGICAL ROBOT AND CONTROLLER OF SURGICAL ROBOT

(71) Applicant: RIVERFIELD INC., Tokyo (JP)

(72) Inventors: Masao Kanazawa, Tokyo (JP); Yasushi Tanaka, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 542 days.

(21) Appl. No.: 17/884,999

(22) Filed: Aug. 10, 2022

(65) Prior Publication Data

US 2022/0378538 A1     Dec. 1, 2022

Related U.S. Application Data

(63) Continuation of application No. PCT/JP2021/001322, filed on Jan. 15, 2021.

(30) Foreign Application Priority Data

Feb. 12, 2020     (JP) ................................. 2020-021628

(51) Int. Cl.
A61B 34/00          (2016.01)
A61B 34/30          (2016.01)
(Continued)

(52) U.S. Cl.
CPC .............. A61B 34/77 (2016.02); A61B 34/25 (2016.02); A61B 34/30 (2016.02); B25J 9/16 (2013.01); A61B 34/76 (2016.02); B25J 13/025 (2013.01)

(58) Field of Classification Search
CPC ......... A61B 34/77; A61B 34/25; A61B 34/30; A61B 34/76; A61B 34/37; A61B 34/74;
(Continued)

(56) References Cited

U.S. PATENT DOCUMENTS 10,013,082 B2     7/2018 Schecter
2007/0021738 A1     1/2007 Hasser et al.
(Continued)

FOREIGN PATENT DOCUMENTS

CN     101642363 A     2/2010
CN     103717170 A     4/2014
(Continued)

OTHER PUBLICATIONS

Notice of Reasons for Refusal of Japanese Application No. 2020-021628 dated Jul. 29, 2020.
(Continued)

*Primary Examiner* — Sohana Tanju Khayer

(74) *Attorney, Agent, or Firm* — Sughrue Mion, PLLC

(57) ABSTRACT

A surgical robot includes a robot arm, an operation device that is operated by a user to perform an operation of the robot arm, an actuator that supplies a driving force to the robot arm, and hardware control logic or a processor that sets a magnitude of an operation reaction force a direction opposite to an operation direction of the operation device, and applies the operation reaction force having the magnitude set by the reaction force setter to the operation device. The magnitude of the operation reaction force is set based on change information about a change in the driving force supplied by the actuator and based on a conversion coefficient.

20 Claims, 8 Drawing Sheets

(51) Int. Cl.
B25J 9/16         (2006.01)
B25J 13/02        (2006.01)

(58) Field of Classification Search
CPC .. A61B 18/1445; A61B 2090/065; B25J 9/16;
B25J 13/025
See application file for complete search history.

(56)                References Cited

U.S. PATENT DOCUMENTS

| | | | |
|---|---|---|---|
| 2009/0088774 A1* | 4/2009 | Swarup | A61B 34/37 |
| | | | 901/31 |
| 2009/0221958 A1 | 9/2009 | Beyar et al. | |
| 2010/0094312 A1 | 4/2010 | Ruiz Morales et al. | |
| 2010/0160728 A1* | 6/2010 | Yoshie | A61B 1/00147 |
| | | | 600/117 |
| 2013/0325029 A1 | 12/2013 | Hourtash et al. | |
| 2014/0018960 A1 | 1/2014 | Itkowitz | |
| 2014/0148819 A1 | 5/2014 | Inoue et al. | |
| 2014/0160015 A1* | 6/2014 | Ogawa | A61B 34/76 |
| | | | 345/156 |
| 2014/0165770 A1 | 6/2014 | Abri et al. | |
| 2014/0195052 A1* | 7/2014 | Tsusaka | A61B 34/30 |
| | | | 700/260 |
| 2015/0066051 A1 | 3/2015 | Kwon et al. | |
| 2016/0332305 A1 | 11/2016 | Gonzalez et al. | |
| 2018/0243897 A1 | 8/2018 | Hasimoto et al. | |
| 2018/0250086 A1 | 9/2018 | Grubbs | |
| 2018/0256271 A1* | 9/2018 | Tojo | B25J 9/161 |
| 2019/0008509 A1 | 1/2019 | Shelton, IV et al. | |
| 2019/0015169 A1 | 1/2019 | Verner et al. | |
| 2019/0060019 A1 | 2/2019 | Maret | |
| 2019/0105117 A1 | 4/2019 | Brisson | |
| 2019/0184576 A1 | 6/2019 | Smith et al. | |
| 2019/0231430 A1 | 8/2019 | Friman et al. | |
| 2019/0328471 A1 | 10/2019 | Tojo et al. | |
| 2020/0022724 A1* | 1/2020 | Worrell | A61B 34/76 |
| 2020/0222138 A1 | 7/2020 | Diolaiti | |
| 2020/0237461 A1 | 7/2020 | Kadokura | |
| 2021/0282795 A1 | 9/2021 | Shimono et al. | |

FOREIGN PATENT DOCUMENTS

| | | | |
|---|---|---|---|
| CN | 104334110 A | 2/2015 | |
| CN | 107921623 A | 4/2018 | |
| CN | 109496143 A | 3/2019 | |
| EP | 2 739 441 B1 | 6/2014 | |
| EP | 3 342 544 A1 | 7/2018 | |
| JP | 4999012 B1 | 8/2012 | |
| JP | 2013-035117 A | 2/2013 | |
| JP | 2014-148037 A | 8/2014 | |
| JP | 2017-512553 A | 5/2017 | |
| JP | 2017-104914 A | 6/2017 | |
| JP | 2019-187994 A | 10/2019 | |
| WO | 2017/033379 A1 | 3/2017 | |
| WO | 2017/098989 A1 | 6/2017 | |
| WO | 2017/220822 A1 | 12/2017 | |
| WO | 2019/017416 A1 | 1/2019 | |

OTHER PUBLICATIONS

Notice of Reasons for Refusal of Japanese Application No. 2020-021628 dated Nov. 2, 2020.
International Search Report of PCT/JP2021/001322 dated Apr. 6, 2021 [PCT/ISA/210].
Office Action dated Apr. 28, 2023 from the Chines Patent Office in Application No. 202180014187.9.
International Preliminary Report on Patentability with the translation of Written Opinion dated Aug. 11, 2022 from the International Bureau in International Application No. PCT/JP2021/001322.

* cited by examiner

53a

OPERATION
DIRECTION

F₁

53a

UP
BACK
RIGHT
LEFT
FRONT
DOWN

SURGICAL ROBOT AND CONTROLLER OF SURGICAL ROBOT

CROSS-REFERENCE TO RELATED APPLICATIONS

This Application is a Continuation of International Application No. PCT/JP2021/001322, filed Jan. 15, 2021, which is based on and claims priority to Japanese Patent Application No. 2020-021628 filed on Feb. 12, 2020 with the Japan Patent Office, the contents of each of which being incorporated by reference herein in their entireties.

BACKGROUND

The present disclosure relates to a surgical robot suitable for use in endoscopic surgery and other surgery.

A surgical robot may be operated by a medical worker such as a doctor and actuated to perform treatments, such as suturing, ablation, and excision, for tissue of a patient. However, some target sites where a treatment is performed using this surgical robot may include tissue easily damaged by an external force. Therefore, there has been a demand for a technology allowing a user to appropriately control a force received by the tissue of the target site from the actuated surgical tools and the arms.

The present disclosure discloses one example of a surgical robot that allows the user to precisely perceive the force received by the tissue of the target site due to actions of the surgical tools and arms of the surgical robot actuated according to the user's operation.

SUMMARY

It is an aspect to provide a surgical robot that allows the user to precisely perceive the force received by the tissue of the target site due to actions of the surgical tools and arms of the surgical robot actuated according to the user's operation.

According to an aspect of one or more embodiments, there is provided a surgical robot comprising an operation part with which a user performs an operation; an action part that performs an action according to the operation; a drive part that supplies a driving force to the action part; and a controller configured to implement at least a reaction force setter that sets a magnitude of an operation reaction force that is a force in a direction opposite to an operation direction of the operation part operated by the user; and a reaction force applicator that applies the operation reaction force having the magnitude set by the reaction force setter to the operation part, wherein when the action part performs the action according to the operation, the reaction force setter sets the operation reaction force based on change information about a change in the driving force supplied by the drive part and a conversion coefficient set in advance.

According to another aspect of one or more embodiments, there is provided controller of a surgical robot, the controller controlling the surgical robot having an operation part and an action part that is actuated according to an operation of the operation part by a user, the controller comprising at least one processor configured to at least set a magnitude of an operation reaction force that is a force in a direction opposite to an operation direction of the operation part that is operated by the user; and apply the operation reaction force to the operation part, the operation reaction force having the magnitude that is set, wherein, when the action part performs the action according to the operation, the at least one processor sets the operation reaction force based on change information about a change in a driving force supplied to the action part by a drive part that supplies the driving force for the action and a conversion coefficient set in advance.

According to yet another aspect of one or more embodiments, there is provided a surgical robot comprising a robot arm; an operation device that is operated by a user to perform an operation of the robot arm; an actuator that supplies a driving force to the robot arm; and hardware control logic or at least one processor configured to at least set a magnitude of an operation reaction force a direction opposite to an operation direction of the operation device; and apply the operation reaction force having the magnitude set by the reaction force setter to the operation device, wherein the magnitude of the operation reaction force is set based on change information about a change in the driving force supplied by the actuator and based on a conversion coefficient.

BRIEF DESCRIPTION OF THE DRAWINGS

The above and/or other aspects will become apparent and more readily appreciated from the following description of various embodiments, taken in conjunction with the accompanying drawings of which.

DETAILED DESCRIPTION

Figure 1:
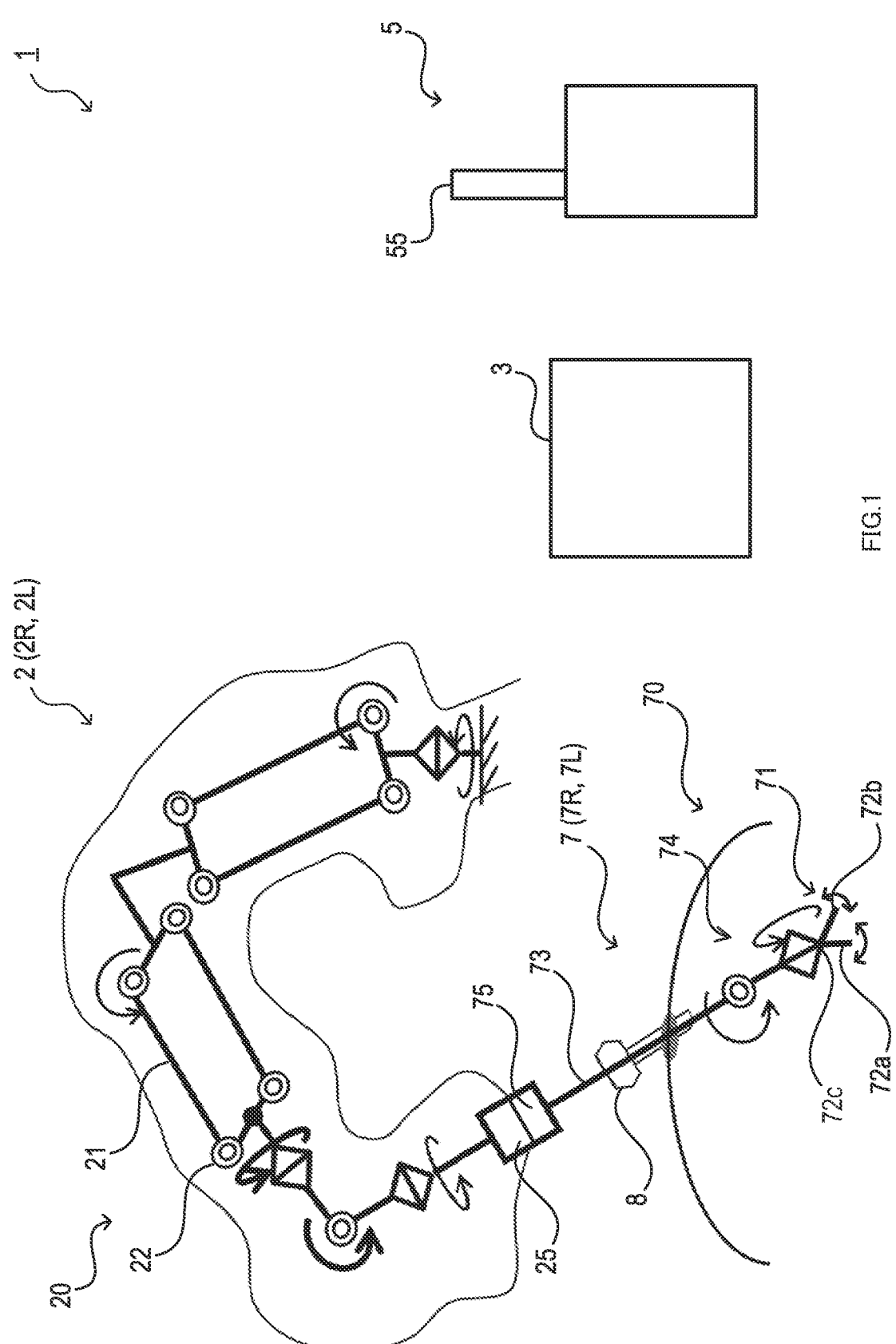
FIG. 1 is a view showing a surgical robot according to some embodiments.

As discussed above, a surgical robot may be operated by a medical worker such as a doctor and actuated to perform treatments, such as suturing, ablation, and excision, for tissue of a patient. Hereinafter, the medical worker who operates the surgical robot is also referred to as "user". This surgical robot includes surgical instruments, such as forceps and electric scalpels to perform medical treatments, and multiple arms supporting the surgical instruments, such as the forceps and the electric scalpels to perform the medical treatments, at desired positions and in desired postures. Hereinafter, the surgical instruments, such as the forceps and the electric scalpels to perform the medical treatments, are also referred to as "surgical tools". The arms supporting the surgical tools and movable parts of the surgical tools are actuated according to the user's operation to perform the treatments for the tissue of the patient.

However, as discussed above, some target sites where a treatment is performed using the surgical robot may include tissue easily damaged by an external force. Therefore, there has been a demand for a technology allowing a user to appropriately control a force received by the tissue of the target site from the actuated surgical tools and the arms.

According to various embodiments, a surgical robot may allow the user to precisely perceive the force received by the tissue of the target site due to actions of the surgical tools and arms of the surgical robot actuated according to the user's operation.

For example, a surgical robot according to an aspect of the present disclosure may include an operation part with which a user performs an operation; an action part performing an action according to the operation; a drive part supplying a driving force to the action part; a reaction force setter setting a magnitude of an operation reaction force that is a force in a direction opposite to an operation direction of the operation part operated by the user; and a reaction force applicator applying the operation reaction force having a magnitude set by the reaction force setter to the operation part, wherein when the action part performs an action according to the operation, the reaction force setter sets the operation reaction force based on change information about a change in the driving force supplied by the drive part and a conversion coefficient set in advance.

In the surgical robot configured in this way, the operation reaction force, which has a magnitude corresponding to the driving force supplied to the action part according to the user's operation, is applied to the operation part. Therefore, the user may operate the surgical robot while perceiving the magnitude of the force received by the tissue of the target site due to the operation.

In another aspect of the present disclosure, the surgical robot may further include an input section receiving an input of information to set the conversion coefficient, and that the reaction force setter may set the operation reaction force based on the change information and the conversion coefficient that is set based on the information received by the input section.

In the surgical robot configured in this way, the user may set the magnitude of the operation reaction force to a magnitude based on a desired rate set by the user. Therefore, for example, depending on the contents of the treatment, the site to be treated and others, the user may arbitrarily set the degree of easiness of perception of the force received by the tissue of the target site.

In another aspect of the present disclosure, the surgical robot may include multiple operation parts and multiple action parts respectively corresponding to the multiple operation parts, and that the reaction force setter may set a magnitude of the operation reaction force for each of the multiple operation parts.

In the surgical robot configured in this way, the user may set the operation reaction force applied to each operation part to have a magnitude based on a rate set for each operation part. Therefore, for example, depending on the contents of the treatment, the site to be treated and others, the user may set, for every operation part, the degree of easiness of perception to perceive the force received by the tissue of the target site.

In another aspect of the present disclosure, the surgical robot may further include an external force detector detecting an external force applied to a specified part of the surgical robot, and that the reaction force setter may set a magnitude of the operation reaction force based on the change information, the conversion coefficient, and a detection signal from the external force detector.

In the surgical robot configured in this way, the user may more accurately perceive the magnitude of the force received by the tissue of the target site due to the user's operation. Even when the surgical tool or other specified part is unintentionally brought into contact with the target site or another part of the patient and a force is applied thereto during the operation, the user may perceive such force.

In another aspect of the present disclosure, the drive part may be a pneumatic actuator, and that the change information may be information about a change in pressure of the pneumatic actuator.

In the surgical robot configured in this way, the user may accurately perceive the magnitude of the force, which is received by the tissue of the target site due to the operation, by the operation reaction force that is set depending on the characteristics of the drive part.

The surgical robot according to various embodiments allows a user to operate the surgical robot while perceiving a magnitude of a force received by tissue of a target site due to the operation.

Various embodiments described below are examples of embodiments that fall within the technical scope of this disclosure. That is, the technical scope of the present disclosure are not limited to the specific configurations, structures, and others shown in the embodiments described below.

Directional arrows, oblique lines, and others in each figure are described to facilitate understanding of the relationship between the figures, and the shape of each member or part. Thus, the technical contents of the present disclosure are not limited to the directions described in each figure. The figures with the oblique lines do not necessarily show sectional views.

At least one member or one part is provided for a member or a part at least described with a reference numeral, except when the member or the part is explicitly described as "one member" or the like. In other words, if there is no mention of "one member" or the like, two or more of such members may be provided. The surgical robot of the present disclosure includes components, such as members and parts at least described with reference numerals, and illustrated structural parts.

Hereinafter, a surgical robot according to some embodiments will be described with reference to FIG. 1 to FIG. 6. In the example of FIGS. 1-6, a description will be made of an example in which the surgical robot is used for endoscopic surgery. In the following description, directions of front-back, left-right, and up-down are directions shown in the figures unless otherwise specified.

<1. Description of Configuration>

As shown in FIG. 1, a surgical robot 1 according to some embodiments may include a first robot arm 2R, a second robot arm 2L, a controller 3, an operation unit 5, a first surgical tool 7R, and a second surgical tool 7L. The first surgical tool 7R may be a surgical tool supported by the first robot arm 2R, and the second surgical tool 7L may be a surgical tool supported by the second robot arm 2L.

In some embodiments, the first robot arm 2R and the second robot arm 2L have the same configuration. The first surgical tool 7R and the second surgical tool 7L have the same configuration. The first robot arm 2R and the second robot arm 2L may have different configurations. The first surgical tool 7R and the second surgical tool 7L may have different configurations.

In the following description, the first robot arm 2R and the first surgical tool 7R will be described. The descriptions of the second robot arm 2L and the second surgical tool 7L, and the illustrations of the second robot arm 2L and the second surgical tool 7L will be omitted. Hereinafter, unless otherwise specified, the first robot arm 2R is also referred to as "robot arm 2", and the first surgical tool 7R is also referred to as "surgical tool 7".

<Surgical Tool>

First, the surgical tool 7 will be described. The surgical tool 7 may be an instrument having a tip side, a part of which is inserted into a body of a targeted person through a trocar 8 perforating in the abdomen or the like of the targeted person undergoing the surgery, thereby performing a treatment for tissue. Hereinafter, the targeted person undergoing the surgery is also referred to as "patient". In some embodiments, a description will be made of an example in which the surgical tool 7 is a pair of forceps commonly used in endoscopic surgery.

The surgical tool 7 may include a grasper 71, a shaft 73 and an adapter 75. The grasper 71 is a part inserted into the patient's body through the trocar 8 to perform a treatment such as grasping of tissue or the like, and the grasper 71 is provided on an end side of the shaft 73. Hereinafter, the side of the shaft 73 where the grasper 71 is provided is also referred to as "tip side" of the shaft 73 or "tip side" of the surgical tool 7.

The shaft 73 is an elongated cylindrical part having the adapter 75 on the opposite side of the grasper 71. The shaft 73 includes a wrist 74 in an area near the grasper 71, and the wrist 74 may be folded in a specified direction or bent in a specified direction around a specified axis. This wrist 74 is a part to change the orientation of the grasper 71 by being folded or bent in a specified direction.

The grasper 71 may include a jaw 72a, a jaw 72b corresponding to the jaw 72a, and a base 72c. The jaw 72a and the jaw 72b are supported by the base 72c so as to be movable closer together and apart from each other.

By the jaw 72a and the jaw 72b moving closer together, the grasper 71 performs an action of grasping the tissue or the like located between the jaw 72a and the jaw 72b. By the jaw 72a and the jaw 72b moving apart from each other, the grasper 71 performs an action of releasing the grasped tissue or the like. Hereinafter, moving the jaw 72a and the jaw 72b closer together is also described as "closing" the grasper 71, and moving the jaw 72a and the jaw 72b apart from each other is also described as "opening" the grasper 71. The action of opening and closing the grasper 71 is also referred to as "open/close action".

Inside the cylindrical shaft 73, unillustrated wires are provided to cause the grasper 71 and the wrist 74 to perform specified actions. In response to a specified tension being applied to the wires, a corresponding part of the grasper 71 or the wrist 74 performs an action according to the tension. Hereinafter, the grasper 71, the wrist 74, and other parts of the surgical tool 7, which are actuated when the specified tension or the like is applied to the wires, are also collectively referred to as "action part of the surgical tool 7" or "action part 70".

<Robot Arm>

The robot arm 2 may be an arm device actuated according to the user's operation to hold the surgical tool 7 in a posture and at a position according to the operation. In other words, the robot arm 2 holds the surgical tool 7 so that a tip portion of the surgical tool 7 is held at a position and in a posture desired by the user. In some embodiments, the grasper 71 is the tip portion of the surgical tool 7.

That is, in response to the user's operation, the robot arm 2 is actuated so that the tip portion of the surgical tool 7, i.e. the grasper 71 is moved in a direction according to the operation. Hereinafter, the direction in which the tip portion of the surgical tool 7 is moved according to the user's operation is also referred to as "direction of movement of the surgical tool 7", or simply referred to as "direction of movement".

The robot arm 2 may include a link mechanism having multiple joint parts 22. That is, the robot arm 2 may include multiple arms 21 connected at the joint parts 22 so that the multiple arms 21 are rotatable in specified directions.

The robot arm 2 includes a connector 25 detachably connecting the surgical tool 7. The adapter 75 of the surgical tool 7 is connected to this connector 25, whereby the surgical tool 7 is supported by the robot arm 2.

Figure 2:
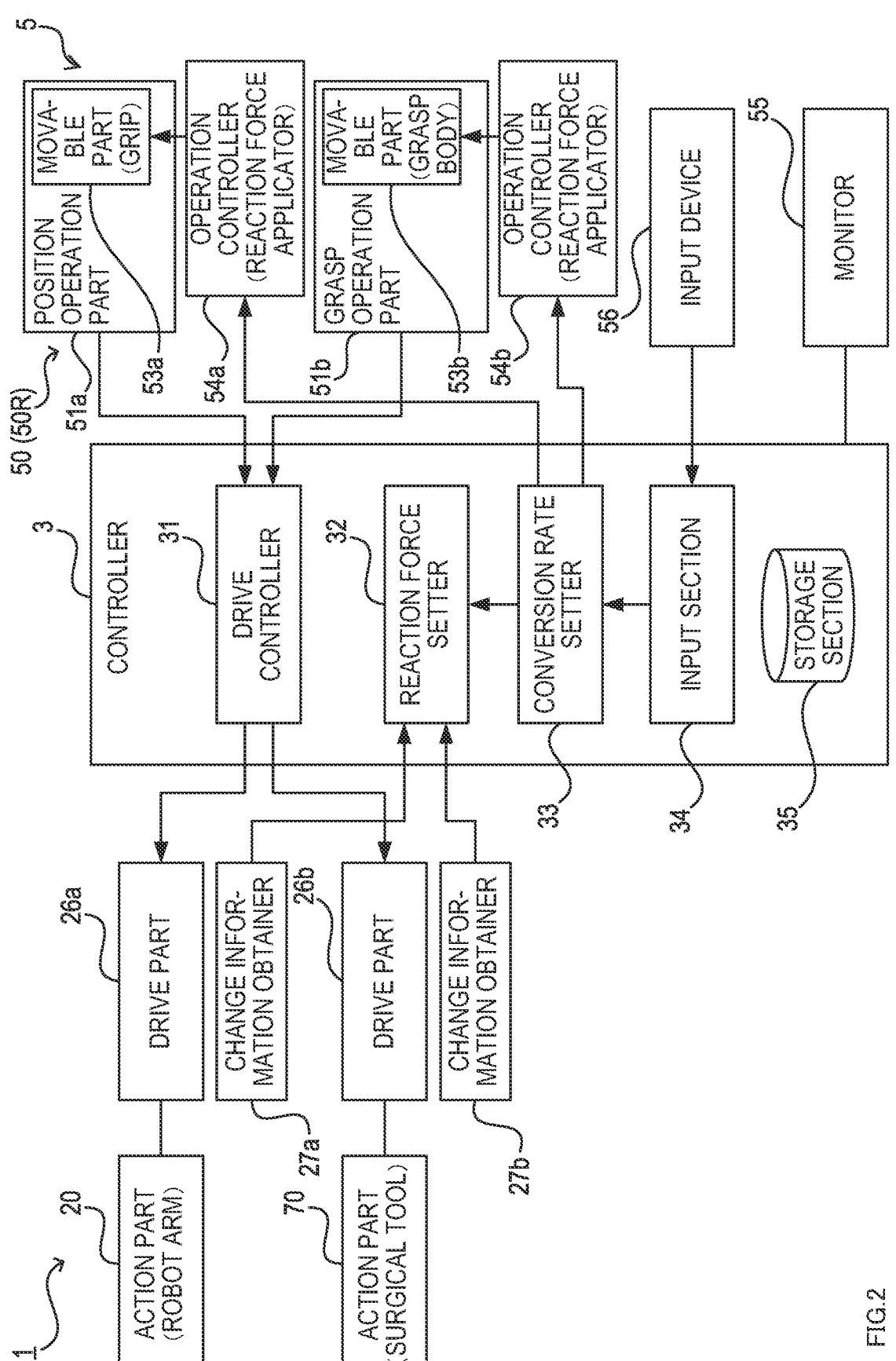
FIG. 2 is a block diagram of the surgical robot illustrated in FIG. 1.

As shown in FIG. 2, the robot arm 2 includes multiple drive parts 26a to cause the arms 21 and/or the joint parts 22 to perform actions according to the user's operation. In FIG. 2, one drive part 26a is described as an example and the descriptions of other drive parts 26a are omitted. The drive part 26a is a part performing physical movement in response to the user's operation to provide a specified driving force to the arm 21 and/or the joint part 22.

In response to the user performing a specified operation with the operation unit 5, the drive part 26a corresponding to the user's operation is actuated to apply a driving force, which has a magnitude corresponding to the user's operation, to the corresponding arm 21 and/or joint part 22. Then, the corresponding arm 21 is rotated around the joint part 22 or moved in a direction according to the user's operation. When the arm 21 and the joint part 22 are actuated in this way, the robot arm 2 is actuated according to the user's operation. Hereinafter, the arm 21 and the joint part 22 that are actuated by the driving force from the drive part 26a are also collectively referred to as "action part of the robot arm 2" or "action part 20". In FIG. 2, for explanation purposes, the arm 21 and the joint part 22 corresponding to one drive part 26a are collectively described as an action part 20, and the descriptions of other arms 21 and joint parts 22 are omitted.

As shown in FIG. 2, the robot arm 2 also includes multiple drive parts 26b applying forces required to cause the grasper 71, the wrist 74, and/or other parts of the surgical tool 7 to perform specified actions. This drive part 26b is a part performing physical movement according to the user's operation to apply a driving force to a specified part of the adapter 75 of the surgical tool 7 to cause the grasper 71 and/or other parts to perform actions according to the user's operation. In FIG. 2, for explanation purposes, one drive part 26b is described as an example and the descriptions of other drive parts 26a are omitted.

In some embodiments, the following description will be made of an example of a configuration in which the drive part 26a and drive part 26b each include a pneumatic actuator. That is, in some embodiments, the drive part 26a and the drive part 26b each may include an unillustrated pneumatic cylinder, a pressure generator that supplies compressed air to the pneumatic cylinder, and a control electromagnetic valve. The drive part 26a and the drive part 26b may each include a force transmission mechanism or other mechanisms that transmits the movement of the pneumatic cylinder to a specified part. The above-described configurations of the drive part 26a and the drive part 26b are examples, and are not limited to the above-described configurations.

The drive part 26a and the drive part 26b respectively include change information obtainers 27a, 27b. The change information obtainers 27a, 27b are air pressure sensors and measure the pressure of the compressed air of the drive parts 26a, 26b respectively when the drive parts 26a, 26b, which are the pneumatic actuators, are actuated. In FIG. 2, the change information obtainers 27a, 27b, which respectively correspond to the drive parts 26a, 26b illustrated as examples, are shown as examples, and the descriptions of other change information obtainers 27a, 27b are omitted.

Hereinafter, the drive parts 26a, 26b are also collectively referred to as "drive part 26", and the change information obtainers 27a, 27b are also collectively referred to as "change information obtainer 27".

<Controller>

As shown in FIG. 2, a controller 3 is a part performing the control of the robot arm 2 and the operation unit 5. In some embodiments, the controller 3 may be implemented by at least one microprocessor or at least one CPU, and in other embodiments, the controller 3 may be implemented by hardware control logic. The controller 3 includes a drive controller 31, a reaction force setter 32, a conversion rate setter 33, an input/receiving section 34, and a storage section 35.

In some embodiments, the controller 3 may be a computer system that has specialized software installed. That is, the specialized software and hardware cooperate to fulfill a function of each section, such as the drive controller 31 and the reaction force setter 32. In the controller 3, each section described below may be implemented by specialized hardware fulfilling its function.

The drive controller 31 is a part controlling the drive part 26 according to an operation signal outputted from the operation unit 5 in response to the user's operation. The reaction force setter 32 is a part setting the magnitude of the operation reaction force that is a force received by the position operation part 51a and the grasp operation part 51b. The position operation part 51a, the grasp operation part 51b, and the operation reaction force will be described below in detail.

The conversion rate setter 33 is a part setting a conversion coefficient used for the setting of the operation reaction force. The input/receiving section 34 is a part receiving information inputted by the user using an input device 56 described below, and also serving as an interface with the input device 56. The input/receiving section 34 is a part receiving information or the like inputted by the user to set a conversion coefficient. The input/receiving section 34 also receives input of information related to the user, the contents of the treatment, the patient, and the contents of the surgery performed by the surgical robot 1, and other information. The input/receiving section 34 is one example of an input section.

The storage section 35 is a storage medium, such as a hard disk or a memory, and is a part storing a program necessary for a process by the controller 3 and storing information or the like related to the settings necessary for the operation of the surgical robot 1.

<Operation Unit>

As shown in FIG. 2, the operation unit 5 is a part with which the user performs operations, and includes a monitor 55, a first operation device 50R, a second operation device 50L, and an input device 56.

Since the configurations, operation methods, and control of the first operation device 50R and the second operation device 50L are the same, hereinafter, the first operation device 50R will be described and the detailed description of the second operation device 50L and the illustration of the second operation device 50L will be omitted. Unless otherwise specified, the first operation device 50R is also referred to as "operation device 50".

The monitor 55 is a monitor device displaying a setting screen for the settings necessary for the operation, an endoscope image of the patient, the states of the robot arm 2 and the surgical tool 7, and/or the indications necessary for the operation of the robot arm 2 and the surgical tool 7. The endoscope image is an image inside the body cavity of the patient, and the image is obtained by an unillustrated endoscope inserted into the body cavity of the patient through an unillustrated other trocar puncturing the abdomen or other part of the patient. This endoscope is held by another robot arm, another endoscope holder, or an endoscope holding apparatus. The above-described other robot arm, the endoscope holder, and the endoscope holding apparatus are not illustrated in FIG. 1 to FIG. 6.

The input device 56 is an input device, such as an unillustrated keyboard, mouse, touch panel or foot switch.

The first operation device 50R is an operation device with which the user operates the first robot arm 2R and the first surgical tool 7R. In other words, the first operation device 50R is a part outputting an operation signal to cause the first robot arm 2R and the first surgical tool 7R to perform actions according to the user's operation.

The second operation device 50L is an operation device by means of which the user operates the second robot arm 2L and the second surgical tool 7L. In other words, the second operation device 50L is a part outputting an operation signal to cause the second robot arm 2L and the second surgical tool 7L to perform actions according to the user's operation.

The operation device 50 includes the position operation part 51a and the grasp operation part 51b. The position operation part 51a is a part operated by the user to change the position of the tip side of the surgical tool 7, or more specifically, the position of the grasper 71. That is, in response to the position operation part 51a being operated, the robot arm 2 is controlled so that the grasper 71 moves in a direction according to the user's operation.

The grasp operation part 51b is a part operated by the user to cause the grasper 71 of the surgical tool 7 to perform an open/close action. That is, in response to the grasp operation part 51b being operated, the robot arm 2 is controlled to cause the grasper 71 to perform the open/close action according to the user's operation. The position operation part 51a or the grasp operation part 51b may be used to operate other parts such as the wrist 74 of the surgical tool 7 by a switching operation of the input device 56 such as a foot switch.

Figures 3A, 3B:
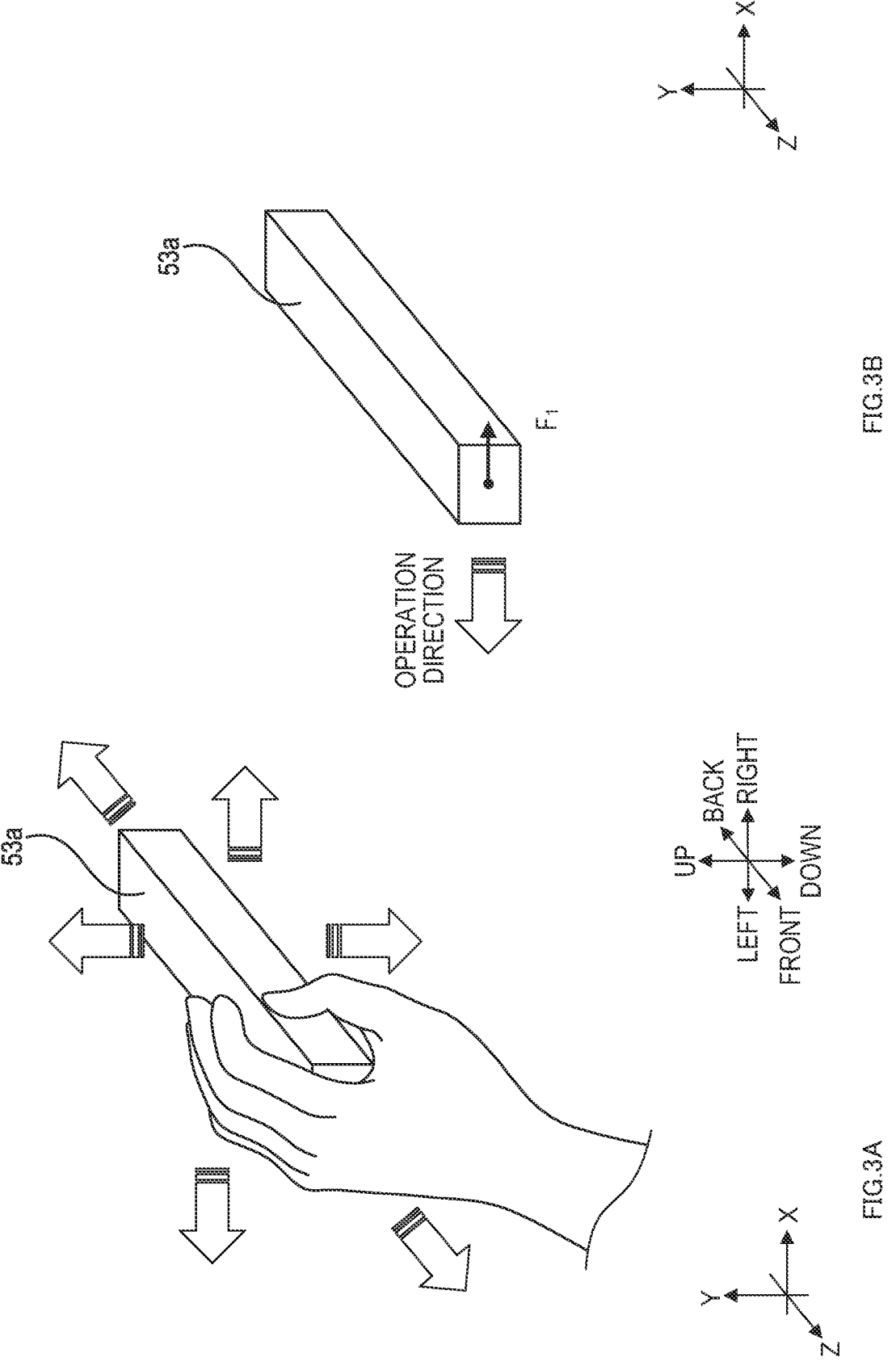
FIGS. 3A-3B are schematic views showing an operation part of the surgical robot according to some embodiments.

In some embodiments, the position operation part 51a is an operation device including a grip 53a supported by an unillustrated support part. The grip 53a is a part that is held by the user during the operation and that is moved in desired directions. As shown in FIG. 3A, the grip 53a is supported by a support part so as to be movable in an up-down direction, a front-rear direction, and a left-right direction, i.e. in an arbitrary three-dimensional direction. Thus, the user may hold the grip 53a and move the grip 53a in the arbitrary three-dimensional direction within a specified range. Hereinafter, with respect to directions in which the grip 53a moves, the up-down direction is referred to as "Y-direction", the left-right direction is referred to as "X-direction", and the front-rear direction is referred to as "Z-direction". In some embodiments, the up-down direction in which the grip 53a moves is also referred to as "Y-axis direction", the left-right direction is also referred to as "X-axis direction", and the front-rear direction is also referred to as "Z-axis direction". The shape of the grip 53a shown in FIG. 3A and FIG. 3B is an example and the shape is not limited to the illustrated shape.

In some embodiments, the grip 53a is supported to be movable in the arbitrary three-dimensional direction by the unillustrated support part including a link mechanism. For the position operation part 51*a*, an operation device having a different configuration may be used as long as the device has a part movable in the arbitrary direction and is suitable for the operation of the robot arm 2.

Figure 4B:
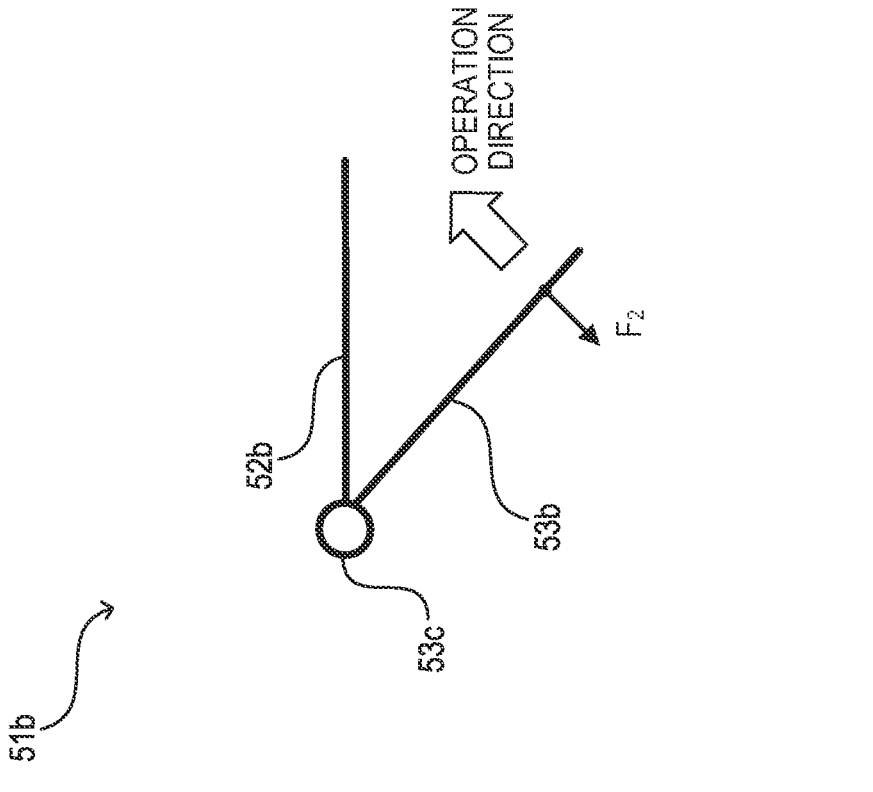
FIGS. 4A-4B are schematic views showing an operation part of the surgical robot according to some embodiments.
Figure 4B:
Figure 4A:
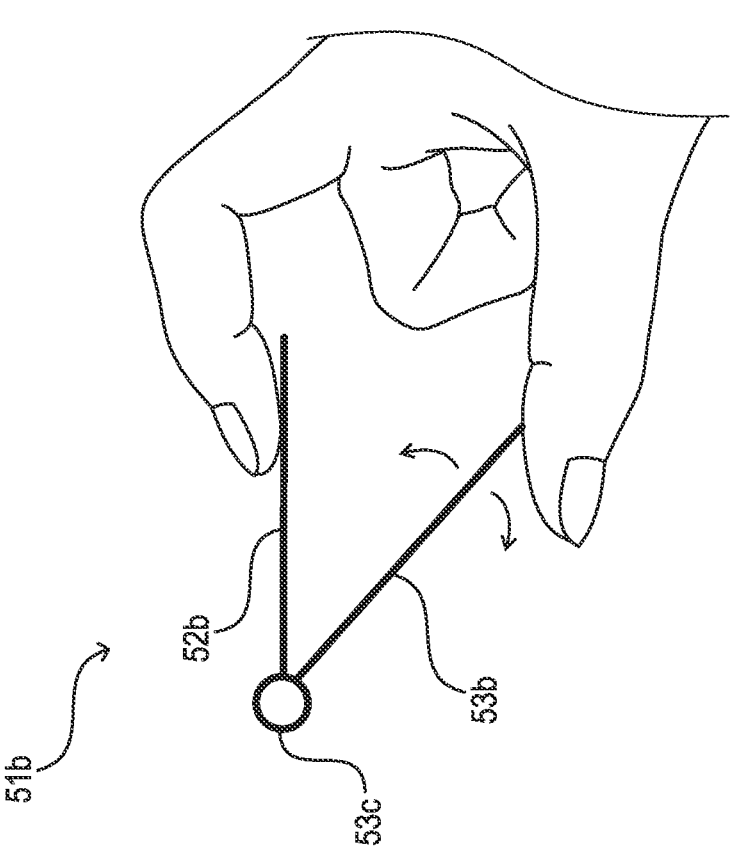

As shown in FIG. 4A and FIG. 4B, the grasp operation part 51*b* of some embodiments is an operation device including a grasp body 53*b* and a support body 52*b* rotatably supporting the grasp body 53*b*. The grasp body 53*b* is supported, at a joint 53*c* provided to the support body 52*b*, so as to be rotatable relative to the support body 52*b*. The shape of the grasp operation part 51*b* shown in FIG. 4A and FIG. 4B is an example and the shape is not limited to the illustrated shape.

As shown in FIG. 4A, the grasp operation part 51*b* is held so that the grasp body 53*b* and the support body 52*b* are held between fingers, such as the thumb and the index finger, of the user to perform the operation of moving the grasp body 53*b* closer to and away from the support body 52*b*. For the grasp operation part 51*b*, an operation device having a different configuration may be used as long as the device has a part movable in a specified direction and the device is suitable for the operation of the grasper 71.

In some embodiments, the grasp operation part 51*b* is provided in an area on a support part 52*a* side of the grip 53*a*, that is, in an area in which the user's fingers are placed when the user holds the grip 53*a*. The grasp operation part 51*b* may be provided in an area different from the above-described area as long as the user may operate the grasp operation part 51*b*.

Hereinafter, the position operation part 51*a* and the grasp operation part 51*b* are also collectively referred to as "operation part 51". The directions in which the grip 53*a* and the grasp body 53*b* are moved by the user's operation are also referred to as "operation direction of the operation part 51", or simply referred to as "operation direction". The grip 53*a* and the grasp body 53*b* are also collectively referred to as "movable part 53".

The position operation part 51*a* is provided with unillustrated multiple sensors, such as encoders, to detect the position of the grip 53*a*. That is, when the grip 53*a* is moved by the user's operation, the position operation part 51*a* outputs operation signals corresponding to a direction of movement and a distance of movement of the grip 53*a* to the drive controller 31.

The grasp operation part 51*b* is also provided with a sensor, such as an encoder, to detect an angle, a distance, or the like between the support body 52*b* and the grasp body 53*b*. Thus, when the user operates the grasp operation part 51*b* and changes the position of the grasp body 53*b*, the grasp operation part 51*b* outputs an operation signal corresponding to the movement of the grasp body 53*b* to the drive controller 31.

The operation device 50 further includes operation controllers 54*a*, 54*b* controlling the movement of the grip 53*a* and the grasp body 53*b*. The operation controllers 54*a*, 54*b* are parts respectively applying operation reaction forces set by the reaction force setter 32 to the position operation part 51*a* and the grasp operation part 51*b*, thereby controlling the forces required to move the grip 53*a* and the grasp body 53*b*.

Specifically, the operation controller 54*a* includes an actuator outputting a force having a magnitude based on a signal from the reaction force setter 32. The operation controller 54*a* also includes a force transmission mechanism to apply the force outputted from the actuator to the grip 53*a* in a direction opposite to the operation direction of the position operation part 51*a*. Similarly, the operation controller 54*b* includes an actuator outputting a force having a magnitude based on a signal from the reaction force setter 32. The operation controller 54*b* also includes a force transmission mechanism to apply the force outputted from the actuator to the grasp body 53*b* in a direction opposite to the operation direction of the grasp operation part 51*b*.

In some embodiments, a description will be made of an example in which the operation controllers 54*a*, 54*b* each include a force transmission mechanism including a pneumatic actuator, a link, a wire, a pulley and other elements. The operation controllers 54*a*, 54*b* may each have a configuration in which an electric actuator, an electric motor, or another actuator is provided as the actuator. The operation controllers 54*a*, 54*b* may be each provided with a force transmission mechanism including a link mechanism or another mechanism. The operation controllers 54*a*, 54*b* are one example of a reaction force applicator.

<Operation Reaction Force>

A description will be made of operation reaction forces that are forces applied by the operation controllers 54*a*, 54*b* to the position operation part 51*a* and the grasp operation part 51*b*.

In surgery using the surgical robot 1, the surgical robot 1 is actuated according to the user's operation and a specified treatment is performed. This operation is made by the user by moving the movable part 53 in a desired direction and for a desired distance. According to this operation, the robot arm 1 and the surgical tool 7 move in a direction and for a distance corresponding to the direction of movement and the distance of movement of the movable part 53.

Here, a force of the user to apply to the movable part 53 for the operation is described as "operation force" to explain. If a force applied by the user to the movable part 53 is larger than the operation force, the movable part 53 moves in the operation direction. Then, the robot arm 2 and the surgical tool 7 are actuated according to the operation direction of the movable part 53. If a force applied by the user to the movable part 53 is less than the operation force, the movable part 53 does not move. That is, the robot arm 2 and the surgical tool 7 are not actuated.

The operation force of the user to move the movable part when the surgical tool or the like is not in contact with the tissue or the like of the patient is described as "operation force during movement" to furthermore explain. As long as the user applies the operation force slightly larger than the operation force during movement to the movable part 53, the robot arm 2 and/or the surgical tool 7 is actuated in a direction corresponding to the operation direction. In other words, for example, even if the surgical tool 7 is already in contact with the tissue of the patient, the robot arm 2 and/or the surgical tool 7 continues to be actuated according to the user's operation unless the user stops the operation. If the robot arm 2 or the surgical tool 7 is actuated in this way, the surgical tool 7 or the like applies a force to the tissue of the patient in contact therewith.

If this applied force is excessive, there is a possibility that the tissue of the patient may be damaged, or the patient may suffer from an undesirable effect. Therefore, the surgical robot 1 of some embodiments has a function to allow the user to perceive a magnitude of the applied force when the tip portion of the surgical tool 7 or the like applies a force to the tissue or the like of the patient. That is, the operation controller 54*a* or 54*b* functions to apply a force, which has a magnitude corresponding to the force applied by the surgical tool 7 or the like to the tissue or the like of the patient, to the movable part 53 of the operation part 51 in a direction opposite to the operation direction thereof. In some embodiments, the force that is applied by the operation controller 54a, 54b to the movable part 53 and that has the magnitude corresponding to the force applied by the surgical tool 7 or the like to the tissue or the like of the patient is referred to as "operation reaction force". In other words, the operation reaction force is a force applied by the operation controller 54a or 54b to the movable part 53 in the direction opposite to the operation direction of the movable part 53 as the driving force outputted from the drive part 26 increases.

More specifically, when the surgical tool 7 is moved and/or the grasper 71 is opened and closed in a state that the surgical tool 7 is not in contact with other parts, the drive part 26 outputs a certain driving force, whereby specified actions are performed. Hereinafter, the driving force in a state that the surgical tool 7 is not contact with other parts is also referred to as "driving force during movement".

On the other hand, when the surgical tool 7 is brought into contact with the patient or the grasper 71 is closed to grip tissue, the drive part 26 needs to output a force larger than the driving force during movement to cause the action part 20 and the action part 70 to perform such actions. Hereinafter, the driving force when the surgical tool 7 is in contact with the patient or the grasper 71 is closed to grip tissue is also referred to as "driving force during treatment".

In the surgical robot 1 of some embodiments, when the drive part 26 is outputting the driving force during treatment, the surgical tool 7 is considered to be in contact with the tissue or the like of the patient, and the operation reaction force is applied to the corresponding movable part 53. Specifically, the reaction force setter 32 sets the magnitude of the operation reaction force based on the amount of change in the driving force and a conversion coefficient set by the conversion rate setter 33. Then, the operation controller 54a or 54b applies the force having the set magnitude to the movable part 53. Here, the conversion coefficient is a coefficient used to set the operation reaction force, and is a coefficient related to the ratio between the force applied by the surgical tool 7 or the like to the tissue or the like of the patient and the operation reaction force.

Thus, when the drive part 26 is outputting the driving force during treatment, the user needs to apply a force at least larger than the operation force during movement to the movable part 53 when moving the movable part 53 for operation. This configuration allows the user to perceive that the surgical tool 7 is in contact with the patient and/or that the grasper 71 is in contact with the target tissue and grasping the target tissue, while operating the operation part 51. The user may also perceive the magnitude of the force applied by the surgical tool 7 or the like to the tissue or the like of the patient.

<2. Details of Control>

Figure 5:
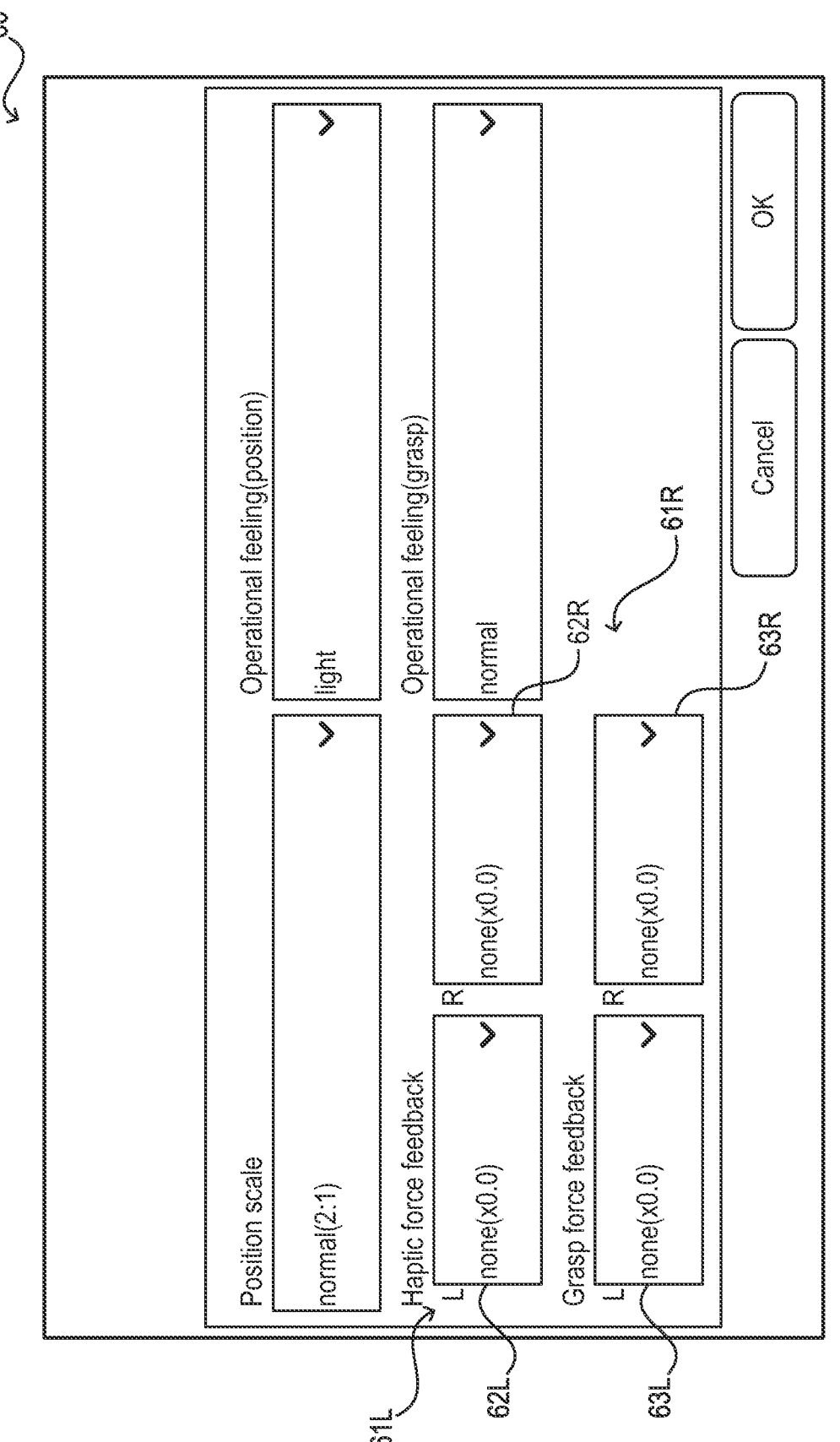
FIG. 5 is a view showing an example of a setting screen of the surgical robot according to some embodiments.
Figure 6:
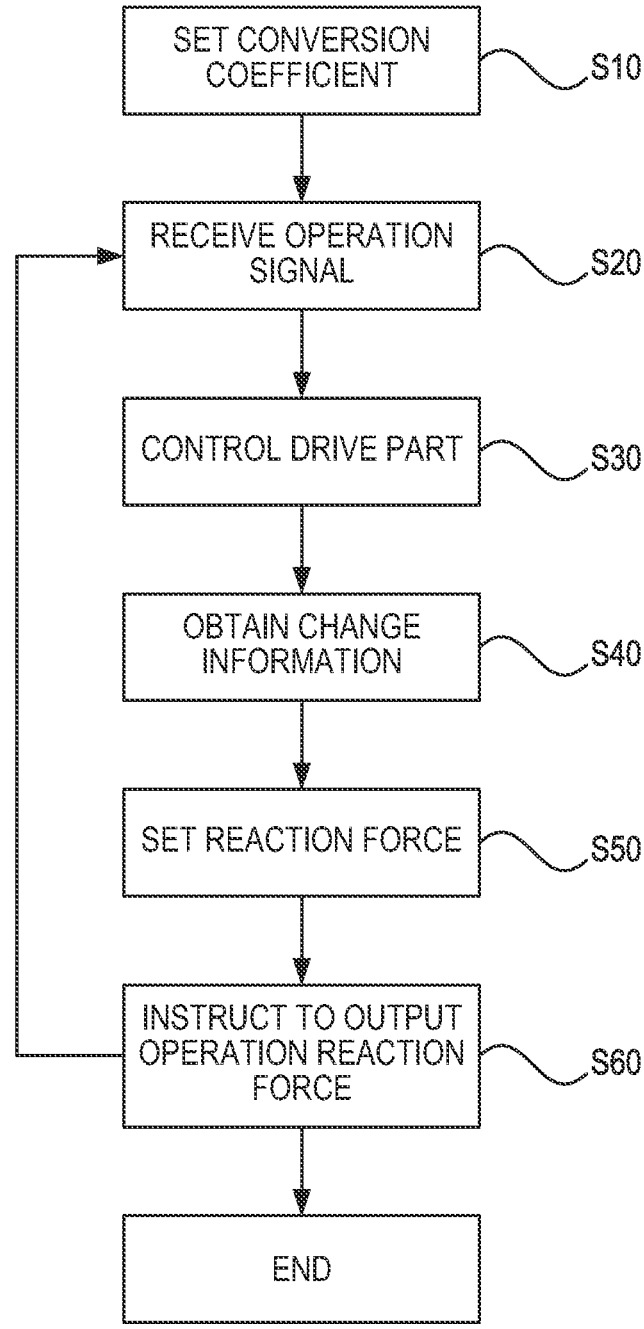
FIG. 6 is a flow diagram showing a process flow by the surgical robot according to some embodiments.

With reference to FIG. 5 and FIG. 6, the control of the surgical robot 1 will be described along a method for operating the surgical robot.

In response to the surgical robot 1 being powered on and a specified operation being performed, the surgical robot 1 starts up. At this time, the input/receiving section 34 receives information, such as user information about the user, information about a patient, and information about a site to be treated, which are inputted by the user according to a specified screen displayed on the monitor 55.

Then, in response to the user further performing a specified operation, a setting screen 60 as shown in FIG. 5 is displayed on the monitor 55. This setting screen 60 includes a first setting field 61R for the settings related to the first operation device 50R and a second setting field 61L for the settings related to the second operation device 50L.

The first setting field 61R and the second setting field 61L respectively include movement conversion coefficient setting fields 62R, 62L to set movement conversion coefficients related to the operation reaction forces applied to the position operation parts 51a, i.e. the grips 53a. The first setting field 61R and the second setting field 61L also respectively include grasp conversion coefficient setting fields 63R, 63L to set grasp conversion coefficients related to the operation reaction forces applied to the grasp operation parts 51b, i.e. the grasp bodies 53b.

In response to the user operating the input device 56 to input desired conversion coefficients in the movement conversion coefficient setting fields 62R, 62L and the grasp conversion coefficient setting fields 63R, 63L, the input/receiving section 34 receives the information. Then, the conversion rate setter 33 sets each conversion coefficient based on the information received by the input/receiving section 34 (S10).

In response to the user operating the operation device 50, the robot arm 2 and the surgical tool 7 are actuated according to the operation. A description will be made of an example in which the user operates the first operation device 50R. In response to the user operating the position operation part 51a, the position operation part 51a outputs an operation signal corresponding to the direction of movement and the distance of movement of the grip 53a to the drive controller 31.

Then, based on the operation signal, the drive controller 31 outputs a signal to the corresponding drive part 26a to output a movement driving force required to move the grasper 71 according to the operation signal (S30). That is, the drive controller 31 outputs a signal to increase the pressure of the drive part 26a, which is a pneumatic actuator, to cause it to output the movement driving force having a specified magnitude. The first robot arm 2R receives this movement driving force and is actuated according to the operation until the part such as the surgical tool 7 or the grasper 71 is brought into contact with the target tissue or the like.

In response to the user operating the grasp operation part 51b, the grasp operation part 51b outputs an operation signal according to the direction of movement of the grasp body 53b to the drive controller 31 (S20). Then, based on the operation signal, the drive controller 31 outputs a signal to the corresponding drive part 26b to cause it to output the driving force required to actuate the grasper 71 (S30).

That is, the drive controller 31 outputs a signal to increase the pressure of the drive part 26b, which is a pneumatic actuator, to cause it to output the driving force during movement having a specified magnitude. The grasper 71 is actuated by the movement driving force outputted from the drive controller 31 until the jaw 72a and the jaw 72b are brought into contact with the target tissue.

When the grasper 71 is moved and brought into contact with the target tissue, a driving force larger than the movement driving force is required to actuate the robot arm 2. That is, the drive part 26a outputs a driving force larger than the movement driving force to cause the robot arm 2 to perform an action based on the operation signal. That is, additional compressed air is supplied from an unillustrated pressure generator, whereby the pressure of the drive part 26a is increased.

In some embodiments, the drive part 26b outputs a driving force larger than the movement driving force to perform a grasping action when the jaw 72a and the jaw 72b are brought into contact with the target tissue. That is, additional compressed air is supplied from an unillustrated pressure generator, whereby the pressure of the drive part 26b is increased.

The reaction force setter 32 detects changes in pressure of the drive part 26a and the drive part 26b based on information from the change information obtainers 27a, 27b (S40). Specifically, the reaction force setter 32 detects an amount of change in pressure of each of the drive parts 26a and 26b when the pressures of the drive parts 26a and 26b are increased compared to the pressures of the drive parts 26a and 26b outputting the movement driving forces. The information about the changes in pressure of the drive parts 26a, 26b detected by the change information obtainers 27a, 27b is one example of change information.

In response to the reaction force setter 32 detecting the changes of the drive parts 26a, 26b, i.e. increases in the pressure, the reaction force setter 32 performs an operation reaction force setting process (S50). Specifically, the reaction force setter 32 calculates the amount of change in pressure of each of the drive parts 26a, 26b based on the signals from the change information obtainers 27a, 27b. Then, this calculated amount of change is multiplied by the conversion coefficient set by the conversion rate setter 33, thereby setting the resultant value as the operation reaction force.

Here, a specific description will be made of an example in which $\Delta Pa$, $\Delta Pb$ are obtained as amounts of change in pressure of the drive parts 26a, 26b, k1 is set as a movement conversion coefficient, and k2 is set as a grasp conversion coefficient. In this case, the reaction force setter 32 sets a value obtained by multiplying $\Delta Pa$ by k1 as the operation reaction force to apply to the position operation part 51a, i.e. the grip 53a. Hereinafter, the reaction force applied to the position operation part 51a is also referred to as "$F_1$". The reaction force setter 32 also sets a value obtained by multiplying $\Delta Pb$ by k2 as the operation reaction force applied to the grasp operation part 51b, i.e. the grasp body 53b. Hereinafter, the reaction force applied to the grasp operation part 51b is also referred to as "$F_2$".

The reaction force setter 32 outputs signals to cause the corresponding operation controllers 54a, 54b to output operation reaction forces having the set magnitudes (S60). Upon receipt of the signals from the reaction force setter 32, the operation controllers 54a, 54b apply the operation reaction forces having the set magnitudes to the grip 53a and the grasp body 53b in the directions opposite to the respective operation directions.

More specifically, as shown in FIG. 3B, the operation controller 54a applies the set operation reaction force $F_1$ to the grip 53a in a direction opposite to the operation direction. Also, as shown in FIG. 4B, the operation controller 54b applies the set operation reaction force $F_2$ to the grasp body 53b in a direction opposite to the operation direction.

In response to the user operating the grasper 71 to move the grasper 71 in a direction releasing the contact between the grasper 71 and the target tissue, the drive controller 31 controls the corresponding drive part 26a to cause it to stop outputting the driving force. That is, the drive controller 31 performs control to reduce the pressure of the drive part 26a.

In some embodiments, in response to the user performing an operation to open the grasper 71 to release the grasped target tissue, the drive controller 31 controls the corresponding drive part 26b to cause it to stop outputting the driving force. That is, the drive controller 31 performs control to reduce the pressure of the drive part 26b. Then, the operation controllers 54a, 54b stop outputting the operation reaction forces.

When the above operation is repeated and the treatment is completed, the process is terminated according to a specified operation by the user.

In the surgical robot 1 of the above-described embodiment, according to the user's operation of the position operation part 51a, an operation reaction force having a magnitude corresponding to the increased amount of the driving force supplied from the drive part 26 is applied to the grip 53a. That is, an operation reaction force having a magnitude corresponding to the increased amount of the pressure of the drive part 26a is applied to the grip 53a. Similarly, according to the user's operation of the grasp operation part 51b, an operation reaction force having a magnitude corresponding to the increased amount of the driving force supplied from the drive part 26b to the grasper 71 is applied to the grasp body 53b. That is, the operation reaction force having a magnitude corresponding to the increased amount of the pressure of the drive part 26b is applied to the grasp body 53b.

Thus, the user may accurately perceive, while operating the surgical robot, the magnitude of the force received by the tissue or the like of the target site due to the user's operation. In other words, the user may perceive the magnitude of the force received by the tissue or the like of the target site through the user's own hands performing the operation. This allows the user to perform an operation in consideration of the magnitude of the force applied by the surgical tool 7 or the like to the tissue or the like of the patient, and to appropriately perform a treatment depending on the site and the state of the target tissue to be treated.

Since the magnitude of the operation reaction force is set based on the amount of change in the air pressure of the pneumatic actuator, more accurate operation reaction force may be set. This allows the user to more accurately know the magnitude of the force received by the tissue or the like of the target site due to the operation. In other words, the user may perceive the magnitude of the force received by the tissue or the like of the target site through the user's own hands performing the operation. In addition, since the pneumatic actuators are used in the drive parts, the surgical robot may move more flexibly.

The conversion coefficient used to set the operation reaction force may be arbitrarily set by the user. Therefore, depending on the contents of the treatment and the site to be treated, for example, the user may arbitrarily set the magnitude of the operation reaction force, i.e. the degree of easiness of perceiving the force received by the tissue of the target site. For example, when a treatment is performed for an area having tissue that could be damaged by the slightest force acting thereon, the user may set large conversion coefficient values to more easily perceive the operation reaction forces. In some embodiments, when a treatment is performed for an area that does not include tissue affected by the applied force, or when it is difficult to operate the grip 53a and the grasp body 53b with the operation reaction forces applied thereto, the user may set small conversion coefficient values to receive small operation reaction forces. That is, the operation reaction force may be set to suitable sensitivities depending on the contents of the treatment. This allows to perform a treatment suitable for the site and the state of the target tissue to be treated, and further allows to provide a surgical robot easy to work with depending on the contents of the treatment.

Furthermore, this conversion coefficient may be individually set for each of the first operation device 50R and the second operation device SOL, and may furthermore be set for each of the position operation parts 51a and the grasp operation parts 51b of the operation devices. Therefore, the conversion coefficient may be flexibly set depending on the site and the state of the target tissue to be treated and the contents of the treatment. For example, when the user uses the right hand to operate the first operation device 50R and the left hand to operate the second operation device 50L, the operation reaction force received by the right hand may be set larger and the operation reaction force received by the left hand may be set smaller, or vice-versa. Thus, for example, the operation reaction force may be set so that the user's dominant hand receives a larger force. Accordingly, settings may be made depending on the user's preference, usability, and circumstances of use.

In some embodiments, suppose that, for example, the second robot arm 2L grasps the target tissue and the first robot arm 2R grasps a suturing needle to perform suturing and the like. The user needs to more accurately perceive, from the grasp operation part 51b operating the surgical tool 7 on a tissue-holding side, the force applied by the grasper 71 to the tissue. On the other hand, it may be unnecessary for the user to perceive the operation reaction force from the grasp operation part 51b operating the grasper 71 holding the suturing needle. In this case, for example, the user may set a larger conversion coefficient value for the grasp operation part 51b of the second operation device 50L, and set a smaller conversion coefficient value for the grasp operation part 51b of the first operation device 50R. That is, it is possible to make settings according to the purposes and contents of the treatment, the user's usability or the like.

Next, a surgical robot 1A will be described with reference to FIG. 7 to FIG. 8.

Figure 7:
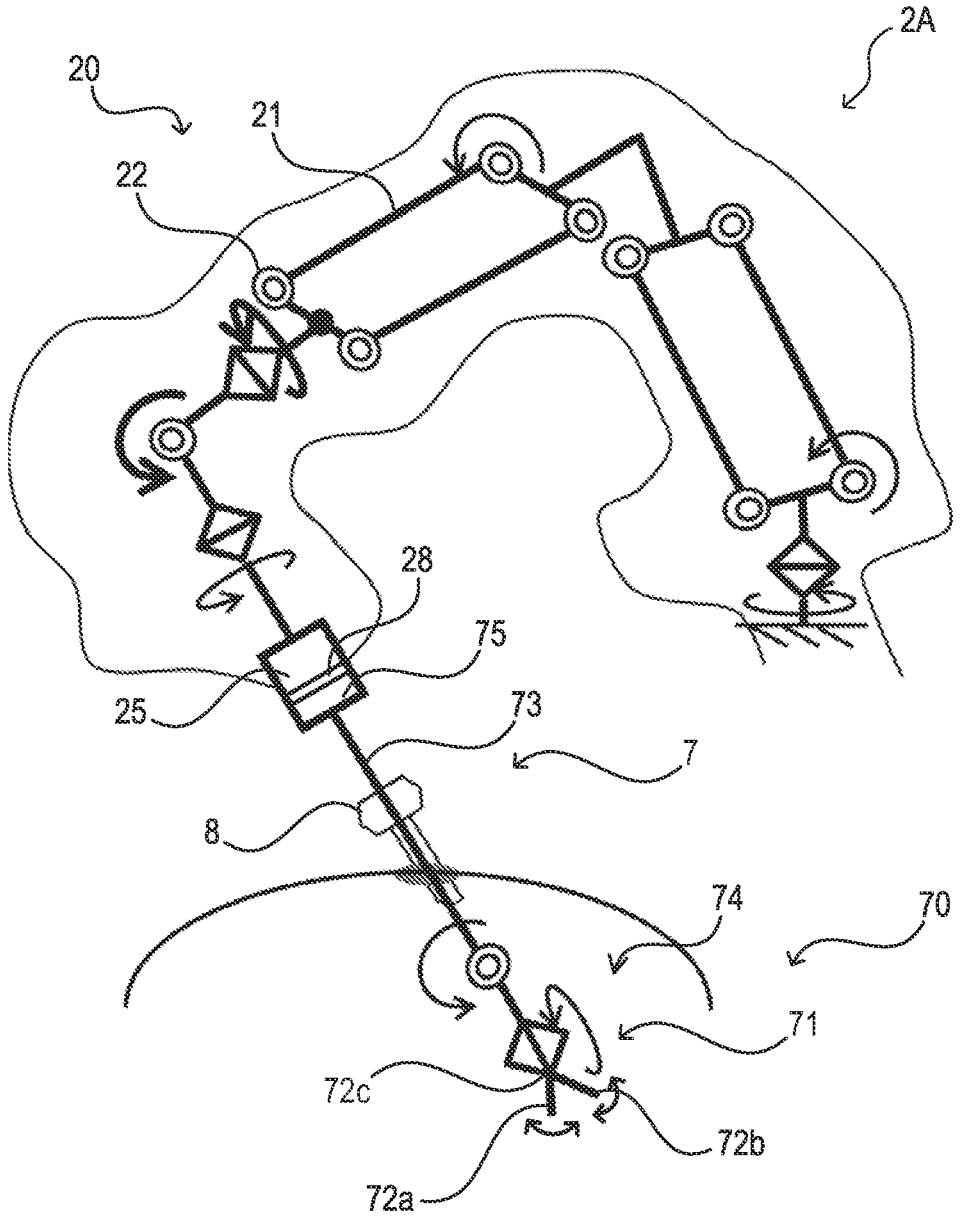
FIG. 7 is a view showing a surgical robot according to some embodiments.
Figure 8:
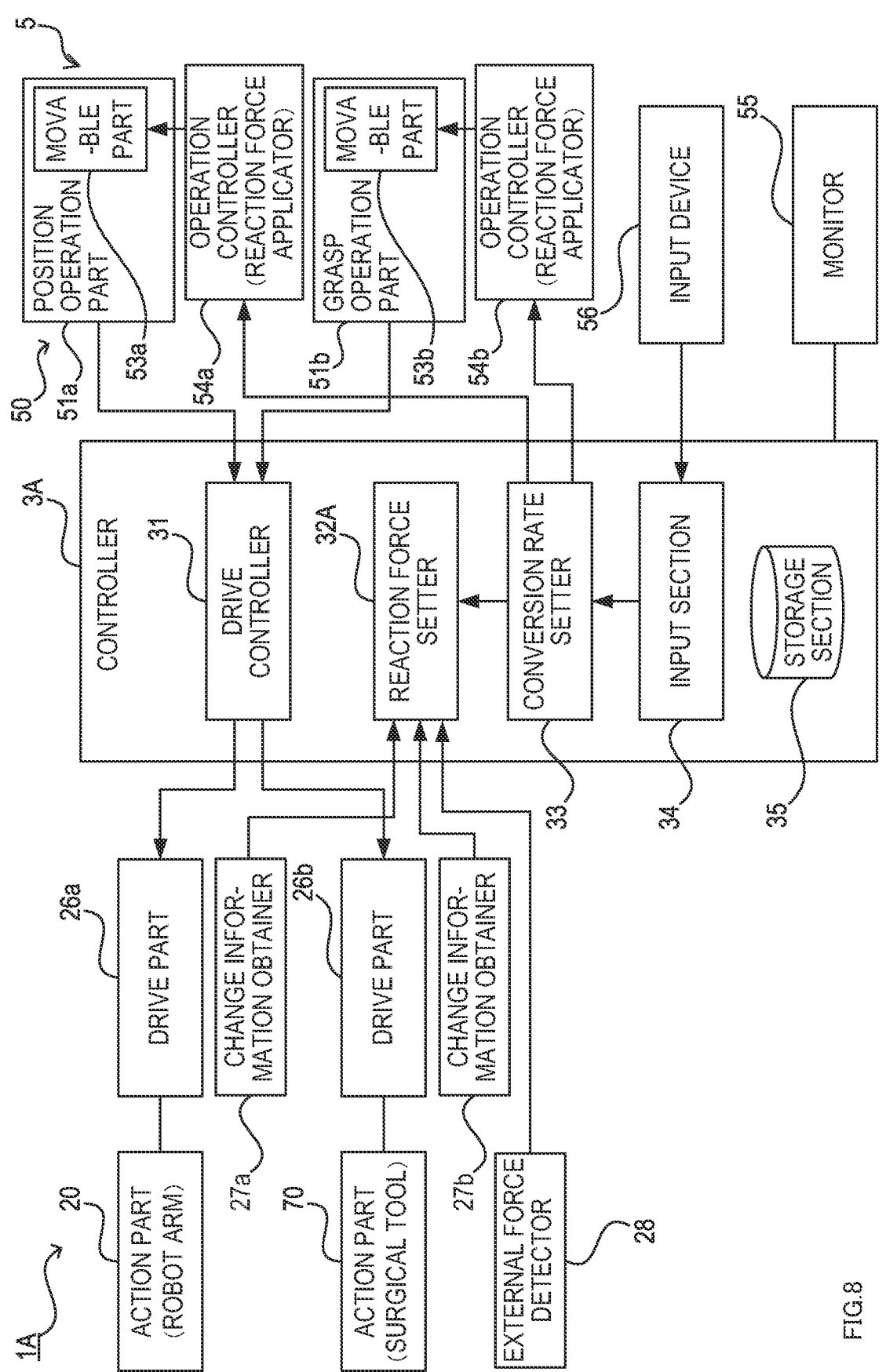
FIG. 8 is a block diagram of the surgical robot of FIG. 7.

The basic structure of the surgical robot 1A of FIGS. 7-8 is similar to that illustrated in FIGS. 1-6. However, the surgical robot 1A is different in that the magnitude of the operation reaction force is set in consideration of a signal from an external force detector 28 as well.

Thus, in some embodiments, differences will be described with reference to FIG. 7 and FIG. 8, and the parts same as those of the first embodiment will be denoted by the same reference numerals, and the descriptions thereof will be omitted.

The robot arm 2A of the surgical robot 1A of some embodiments includes, as shown in FIG. 7 and FIG. 8, the external force detector 28 detecting an external force that is externally applied to the shaft 73 of the surgical tool 7. Here, the external force means the force, which is applied to the shaft 73 because of a contact between a part of the surgical tool 7 and a part other than the surgical tool 7. In some embodiments, the external force detector 28 is arranged in a region between the connector 25 and the adapter 75. The external force detector 28 may be arranged in another region.

That is, the external force is the force received by the shaft 73 when, for example, the shaft 73 comes in contact with the trocar 8 or the like, or when the tip portion or another part of the shaft 73 comes in contact with the tissue or the like of the patient. In some embodiments, the external force means the force received by the shaft 73 when another part of the surgical tool 7 comes in contact with the trocar 8, the tissue of the patient, and/or other parts.

The external force detector 28 is a force sensor capable of detecting a magnitude and a direction of the applied force. As the external force detector 28, a force torque sensor or the like detecting the magnitudes of force and torque may be used. However, other sensors may be used as long as these sensors are capable of detecting the external force applied to the shaft 73.

The reaction force setter 32A of some embodiments has a function to set an operation reaction force based on information from the change information obtainers 27a, 27b, conversion coefficients set by the conversion rate setter 33, and furthermore, a detection signal from the external force detector 28. That is, the reaction force setter 32A sets the operation reaction force based on the information about the amount of change in pressure of each of the drive parts 26a, 26b obtained by the change information obtainers 27a, 27b and information about the external force from the external force detector 28.

Specifically, the reaction force setter 32A obtains a magnitude of force $F_3$ obtained based on the information about the amount of change in pressure of each of the drive parts 26a, 26b, and a magnitude of force $F_4$ in the direction corresponding to the operation direction of the external force, which is determined from the information about the external force obtained by the external force detector 28. Then, a value obtained by adding the obtained two forces, i.e. $F_3+F_4$ is multiplied by a conversion coefficient, whereby an operation reaction force is set. The reaction force setter 32A may set, as the operation reaction force, values obtained by multiplying respective forces, i.e. $F_3$ and $F_4$ by different conversion coefficients. In some embodiments, the operation reaction force may be set by other methods based on the information about the amount of change in pressure of each of the drive parts 26a, 26b, the information about the external force from the external force detector 28, and the conversion coefficient.

The reaction force setter 32A outputs signals to cause the operation controllers 54a, 54b to output the set operation reaction forces, and the operation controllers 54a, 54b respectively apply the corresponding operation reaction forces to the grip 53a and the grasp body 53b.

With the surgical robot 1A having the above-described configuration, the reaction force setter 32A sets the operation reaction force in consideration of the information from the external force detector 28 as well. Therefore, the user may more accurately know the force acting on the tissue of the target site due to the operation, i.e. the magnitude of the force that the surgical tool 7 or the like applies to the tissue or the like of the patient.

In addition, when performing an operation, even if the shaft 73 or the like of the surgical tool 7, for example, comes in contact with the trocar 8 or the like and an unintentional force acts on the patient, the user may perceive such a state while performing the operation. In some embodiments, if another part of the surgical tool 7 comes in contact with a part of the patient and an unintentional force acts on the patient, the user may perceive such a state when performing the operation. In some embodiments, even if another force that cannot be calculated from the amount of change in pressure of each of the drive parts 26a, 26b is applied to the shaft 73, the user may perceive such a state while performing the operation.

That is, the user may more accurately perceive the force acting on the shaft 73, and thus, the user may more accurately perceive the magnitude of the force received by the target tissue and the patient. Therefore, the surgical robot allows to perform an appropriate treatment depending on the site of the target tissue to be treated and the state of the tissue. In a case where a part other than the tip portion of the surgical tool 7 unintentionally comes in contact with the patient, the user may quickly perceive such unnecessary contact, and may perform an operation to avoid such contact.

The technical scope of the present disclosure is not limited to the above embodiments, and various modifications may be made without departing from the gist of the disclosure. For example, in the above embodiments, a description has been made of a case where the drive part 26 may include a pneumatic actuator. However, the drive part 26 may have a configuration in which an electric actuator or an electric motor is used. For the change information obtainers 27a, 27b, power sensors, ammeters, or other devices detecting the power or current supplied to the electric motor may be used. A configuration may be adopted in which the reaction force setter 32 calculates the amount of change in the driving force outputted from the drive part 26 based on the amount of change in the electricity supplied to the drive part 26 and sets the operation reaction force based on the calculated value.

A configuration may also be adopted in which the external force detector 28 is arranged so as to detect the force acting on a part other than the shaft 73 of the surgical tool 7. In some embodiments, a configuration may also be adopted in which an external force detector 28 is further provided to detect the force acting on a specified part of the robot arm 2. In this way, for example, in a case where other parts of the robot arm 2 and/or the surgical tool 7 come in contact with the patient or the like and apply unnecessary force to the patient or the like, the user may know such a state.

In the above-described embodiments, the description has been applied to an example in which the surgical tool 7 is a pair of forceps. However, the surgical tool 7 may, for example, include an electric scalpel, a stapler, or another tool that is used in endoscopic surgery and that is arranged at the tip side of the shaft 73.

In the above-described embodiments, the description has been made of an example in which the surgical robot 1 is used in endoscopic surgery. The surgical robot 1 may be used, for example, in other fields of surgery or treatment for patients, such as neurosurgery or cardiovascular surgery.

For example, for each field and/or site of surgery, for which the surgical robot 1 is used, corresponding conversion coefficients may be set in advance, and combinations of the conversion coefficients corresponding to the field and/or site of surgery may be stored in the storage section 35. The conversion rate setter 33 may then refer to the storage section 35 based on the information about the field and/or site of surgery, which is received by the input/receiving section 34, and acquire the corresponding conversion coefficients, thereby setting them as the conversion coefficients used to set the operation reaction forces. In this way, simply by, for example, selecting the site of surgery and the field of surgery, the conversion coefficients suitable for the site and the field of surgery may be set, making the surgical robot easy to set the conversion coefficients.

In some embodiments, the conversion coefficients may be set in advance for each user, and the combination of the user information about the user and the conversion coefficients set in advance may be stored in the storage section 35. The conversion rate setter 33 may then refer to the storage section 35 based on the information about the user information, which is received by the input/receiving section 34, and acquire the corresponding conversion coefficients, thereby setting them as the conversion coefficients used to set the operation reaction forces. In this way, if the user simply enters the user's own information, the conversion coefficients suitable for the user may be set, making the surgical robot easy to set the conversion coefficients.

Various embodiments have been described above with reference to the drawings. However, it is to be understood that the present disclosure is not limited to the above embodiments, but various changes and modifications may be made therein without departing from the spirit and scope thereof as set forth in appended claims.

What is claimed is:

1. A surgical robot comprising:
a grip with which a user performs an operation;
a robot arm that performs an action according to the operation and comprising an actuator mounted thereon that supplies a driving force to the robot arm to perform the action; and
a controller configured to implement at least:
a reaction force setter that sets a magnitude of an operation reaction force that is a force in a direction opposite to an operation direction of the grip operated by the user; and
a reaction force applicator that applies the operation reaction force having the magnitude that is set by the reaction force setter to the grip,
wherein when the robot arm performs the action according to the operation, the reaction force setter sets the operation reaction force based on change information about a change in the driving force supplied by the actuator to perform the action and a conversion coefficient that is set in advance.

2. The surgical robot according to claim 1, wherein the controller is further configured to implement an input section that receives an input of information to set the conversion coefficient, and
wherein the reaction force setter sets the operation reaction force based on the change information and the conversion coefficient that is set based on the information received by the input section.

3. The surgical robot according to claim 1,
wherein the grip is provided in plural, and the robot arm is provided in plural respectively corresponding to the plurality of grips, and
wherein the reaction force setter sets a magnitude of the operation reaction force for each of the plurality of grips.

4. The surgical robot according to claim 1, further comprising an external force detector that detects an external force applied to a specified portion of the surgical robot,
wherein the reaction force setter sets the magnitude of the operation reaction force based on the change information, the conversion coefficient, and a detection signal from the external force detector.

5. The surgical robot according to claim 1,
wherein the actuator comprises a pneumatic actuator, and
wherein the change information is information about a change in pressure of the pneumatic actuator.

6. A controller of a surgical robot, the controller controlling the surgical robot having a grip and a robot arm that is actuated, by an actuator of the robot arm mounted thereon, according to an operation of the grip by a user, the controller comprising at least one processor configured to at least:
set a magnitude of an operation reaction force that is a force in a direction opposite to an operation direction of the grip that is operated by the user; and
apply the operation reaction force to the grip, the operation reaction force having the magnitude that is set,
wherein, when the robot arm performs an action according to the operation, the controller sets the operation reaction force based on change information about a change in a driving force supplied to the robot arm by the actuator that supplies the driving force to perform the action and based on a conversion coefficient that is set in advance.

7. The controller according to claim 6, wherein the controller receives an input of information to set the conversion coefficient, and wherein the controller sets the operation reaction force based on the change information and the conversion coefficient that is set based on the information.

8. The controller according to claim 6, wherein the grip is provided in plural, and the robot arm is provided in plural respectively corresponding to the plurality of grips, and wherein the controller sets a magnitude of the operation reaction force for each of the plurality of grips.

9. The controller according to claim 6, further comprising an external force detector that detects an external force applied to a specified portion of the surgical robot, wherein the controller sets the magnitude of the operation reaction force based on the change information, the conversion coefficient, and the external force.

10. The controller according to claim 6, wherein the actuator comprises a pneumatic actuator, and wherein the change information is information about a change in pressure of the pneumatic actuator.

11. A surgical robot comprising:

a robot arm comprising an actuator mounted thereon that supplies a driving force to the robot arm to perform an action;

a grip that is operated by a user to perform an operation of the robot arm; and hardware control logic or at least one processor configured to at least:

set a magnitude of an operation reaction force in a direction opposite to an operation direction of the grip; and apply the operation reaction force having the magnitude, to the grip, wherein, when the robot arm performs the action according to the operation, the magnitude of the operation reaction force is set based on change information about a change in the driving force supplied by the actuator to perform the action and based on a conversion coefficient.

12. The surgical robot according to claim 11, wherein the magnitude of the operation reaction force is set when the robot arm performs an action according to the operation.

13. The surgical robot according to claim 11, wherein the conversion coefficient is set and stored in advance.

14. The surgical robot according to claim 11, wherein the hardware control logic or the at least one processor receives information to set the conversion coefficient, and stores the conversion coefficient based on the information.

15. The surgical robot according to claim 11, wherein the grip moves a surgical tool attached to the robot arm in a first direction, and a grasp body that moves the surgical tool in a second direction that is different from the first direction.

16. The surgical tool according to claim 15, wherein the surgical tool comprises a grasper, and the grip changes a position of a tip of the grasper, and the grasp body cause the grasper to move in an open/close action.

17. The surgical robot according to claim 11, wherein the grip is provided in plural, and the robot arm is provided in plural corresponding respectively to the plurality of grips, and wherein the magnitude of the operation reaction force is set for each of the plurality of grips.

18. The surgical robot according to claim 11, further comprising a force sensor that detects an external force applied to a specified portion of the surgical robot, wherein the hardware control logic or the at least one processor sets the magnitude of the operation reaction force based on the external force.

19. The surgical robot according to claim 11, wherein the actuator comprises a pneumatic actuator, and wherein the change information comprises information about a change in pressure of the pneumatic actuator.

20. The surgical robot according to claim 11, wherein the hardware control logic or at least one processor is further configured to detect the change in the driving force supplied by the actuator to perform the action, and set the magnitude of the operation reaction force based on the detected change and the conversion coefficient.

\* \* \* \* \*